United States Patent [19]
Gildenberg

[11] Patent Number: 5,961,456
[45] Date of Patent: *Oct. 5, 1999

[54] SYSTEM AND METHOD FOR DISPLAYING CONCURRENT VIDEO AND RECONSTRUCTED SURGICAL VIEWS

[76] Inventor: Philip L. Gildenberg, 3776 Darcus St., Houston, Tex. 77005

[ * ] Notice: This patent issued on a continued prosecution application filed under 37 CFR 1.53(d), and is subject to the twenty year patent term provisions of 35 U.S.C. 154(a)(2).

[21] Appl. No.: 08/625,572

[22] Filed: Mar. 28, 1996

Related U.S. Application Data

[63] Continuation-in-part of application No. 08/395,770, Feb. 28, 1995, abandoned, and a continuation-in-part of application No. 08/552,168, Nov. 2, 1995, abandoned, said application No. 08/395,770, is a continuation of application No. 08/060,562, May 12, 1993, abandoned, said application No. 08/552,168, is a continuation of application No. 08/303,862, Sep. 9, 1994, abandoned, which is a continuation-in-part of application No. 08/060,562, abandoned.

[51] Int. Cl.$^6$ .......................................... A61B 5/00
[52] U.S. Cl. ........................... 600/429; 600/426; 600/476; 606/130
[58] Field of Search .................................. 128/653.1, 665; 606/130; 600/425, 429, 476, 426, 414, 417

[56] References Cited

U.S. PATENT DOCUMENTS 5,389,101 2/1995 Heilbrun et al. ...................... 128/653.1
5,662,111 9/1997 Cosman .................................. 600/429

Primary Examiner—Ruth S. Smith
Attorney, Agent, or Firm—Vinson & Elkins, L.L.P.

[57] ABSTRACT

A video camera is positioned stereotactically to view a surgical opening in a patient and provide data related to stereotactic space and is stereotactically representative of a current view, which data is processed and displayed as a current actual image along with a reference image that is computer generated from graphics image data stored on the patient. The two images appear in a display variously, for ease of comparison and are coordinated by stereotactically tracking the camera to maintain position and orientation. A composite camera structure incorporates a surgical microscope and stereoscopic viewing along with light tracking coordination. Displays included side-by-side and overlapped.

19 Claims, 2 Drawing Sheets

SYSTEM AND METHOD FOR DISPLAYING CONCURRENT VIDEO AND RECONSTRUCTED SURGICAL VIEWS

CROSS-REFERENCE TO RELATED APPLICATIONS

This is a continuation-in-part of application Ser. Nos. 08/395,770 now abandoned and 08/552,168 now abandoned, filed on Feb. 28, 1995, and Nov. 2, 1995, respectively, and both entitled "CAMERA SYSTEM AND COMPUTER GRAPHIC DISPLAY FOR VIDEO AND IMAGE RECONSTRUCTED SURGICAL VIEWS", application Ser. No. 08/395,770, is a continuation of application Ser. No. 08/060,562, filed on May 12, 1993, and entitled "CAMERA SYSTEM AND COMPUTER GRAPHIC DISPLAY FOR VIDEO AND IMAGE RECONSTRUCTED SURGICAL VIEWS", now abandoned, and application Ser. No. 08/552,168, is a continuation of application Ser. No. 08/303,862, filed on Sep. 9, 1994, and entitled "CAMERA SYSTEM AND COMPUTER GRAPHIC DISPLAY FOR VIDEO AND IMAGE RECONSTRUCTED SURGICAL VIEWS", now abandoned, which is a continuation-in-part of application Ser. No. 08/060,562 now abandoned.

BACKGROUND AND SUMMARY OF THE INVENTION

The use of stereotactic instrumentation based on tomographic imaging is now common place in surgery, especially in neurosurgery of the brain. Such methods typically involve attaching a headring apparatus to the patient's skull and acquiring imaging data that is space related to the headring, for example, by the utilization of indexing devices, localizer structure or other fiducial apparatus. Thus, quantitative coordinates of targets within the patient's head can be specified relative to the fiducial apparatus. An arc system or other pointing device then can be used to guide probes or other instruments selectively into the brain quantitatively based on the imaging data.

Also common place in prior techniques is the acquisition and use of large, three-dimensional data sets of imaging data that is stored in computer graphics workstations and visualized on computer graphics screens, such as cathode ray tube (CRT) screens in an operating room. Computer graphics data has been used in conjunction with other apparatus. For example, computer graphics images, based on imaging data have been placed in the direct view field of a surgical microscope. Specifically, see U.S. Pat. No. 4,722,056 granted Jan. 26, 1988 to Roberts et al. Also, to some extent, computer graphic methods have been used with stereotactic arc systems. For example, the work of Dr. Patrick Kelly (Tumor Stereotaxis) referred to in the referenced patent to Roberts et al is pertinent in that regard. Accordingly, a graphic representation of a surgical approach into the head is displayed on a computer screen based on reconstructed images of tomographic scan data. Thus, by knowing the quantitative stereotactic direction into the surgical area, a corresponding graphics display image can be displayed on a computer screen. Consequently, a surgeon can view a reconstructed picture of the image he will see upon looking directly into an actual surgical field, either with a naked eye or through a microscope. Quantitative maneuvers, such as volumetric resection, can thus be made by measurements in the actual surgical field, compared to measurements extracted from the graphic display.

Generally, computer-assisted stereotactic surgery is becoming popular in neurosurgery. In that regard, examples of various available computer graphic systems for use in surgery are produced by Radionics/RSI, Burlington, Mass. A system known as the Compass System is a commercial product embodying Dr. Kelly's technique as mentioned above. Another specific implementation of Dr. Kelly's technique involves importing a reconstructed graphics image into a "heads-up" display, which the surgeon can see as he views the surgical field directly or through a surgical microscope. Forms of heads-up displays, using goggles, are common place in military aircraft applications. Accordingly, a small display can indicate a computer-reconstructed image of what should be seen in a surgical field. Thus, the surgeon can view directly the surgical field and make decisions and quantitative maneuvers in the surgery, based on comparison with the heads-up display.

Generally, these prior computer-assisted surgical methods have certain disadvantages. In the screen display apparatus, the surgeon must view the computer graphics screen, then change his view to the surgical opening. Accordingly, an inconvenient two-step operation is involved requiring alternate viewing. In the case of the heads-up displays, (as for example through a microscope as described by Kelly, stated below) the surgeon is encumbered by having to wear goggles or visualize only a rudimentary outline of the target volume.

The Kelly technique imparting an image, based on a computer-generated target, into visualization of a surgical field, ordinarily involves a microscope. The technique restricts the target image to a rudimentary outline and restricts the view line to the target volume. It is also noteworthy that surgery, while looking at a graphic display (video) is commonly performed in other fields employing endoscopic techniques, however, those techniques do not relate a video image to a computer graphics display.

Generally, the present invention involves stereotactically mounting a video camera to provide image data. Thus, plural surgical images can be provided, as for comparison, in a single (or plural) computer graphics display, one, the surgical view image, the other, a reconstructed image from graphics data. The surgical view image for the single display may be accomplished using a minimally invasive, extracorporeal camera located outside the body near the surgical opening. Thus, in accordance herewith, the camera structure providing the video (actual image) related to stereotactic space, in one embodiment, may be minimally obtrusive so that the surgeon can view into the surgical field directly by naked eye, or by microscopic view. The surgical view or actual current image is combined in accordance with one embodiment in a common unitary display with the reconstructed or reference image processed from computer graphics data. The comparable images in a single display are enabled by tracking and correlating the position of the camera to the patient (camera subject). Thus, for example, by the utilization of stereotactic placement or registration of camera positions and patient anatomy, effective dual images (current actual and reference) may be provided in a single display. For example, a video image may be displayed on a single display means along with a reconstructed computer graphics image provided from prescanned or imaged data. Alternatively, the surgical view or actual current image and the reconstructed or reference image may be provided in plural displays.

BRIEF DESCRIPTION OF THE DRAWINGS

In the figures, which constitute a part of this specification, exemplary embodiments exhibiting various subjectives and features hereof are set forth, specifically.

DESCRIPTION OF THE ILLUSTRATIVE EMBODIMENTS

Figure 1:
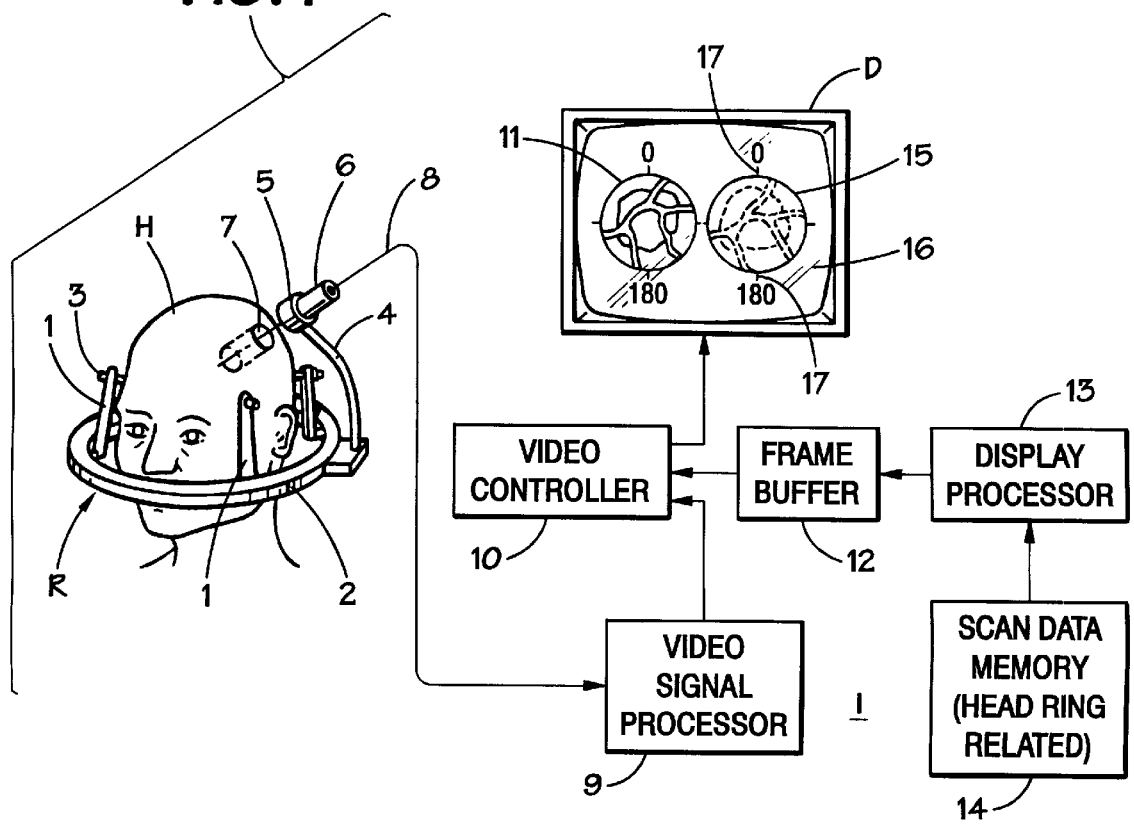
FIG. 1 is a combined perspective and block diagram view showing an embodiment of the present invention.

FIG. 1 shows a patient's head H with a surgical platform or headring apparatus R fixed to the patient's skull. In such an environment, an imaging system I receives video and position data to drive a display apparatus D depicting two surgical views as illustrated. As disclosed in detail below, an actual current image is displayed along with a reference view provided from computer graphics data.

Considering the structure of the imaging system I in greater detail, the headring apparatus R is fixed to the patient's head H by headposts 1 extending upward and somewhat axially parallel from a ring 2 and terminating at headscrews 3. Generally, the headring apparatus R typifies well known stereotactic structures involving the utilization of well known stereotactic reference methods. The headring 2 also carries an adjustable holder 4 (sometimes referred to as a localizer) which includes an adaptor 5 fitted to receive a small video camera 6. Note that the video camera 6 is positioned to view into the depths of a surgical opening 7 in the patient's head H.

The video camera 6 is connected by a cable 8 to a video signal processor 9, which functions in cooperation with the camera 6 to produce a video signal as well known in the art. The processor 9 is in turn coupled to a video controller 10 which also receives signals representative of a second image. However, at this point it is to be understood that as one component, the controller 10 provides a signal to the display device D for picturing the camera view, e.g., the image 11 (left).

The video controller 10 may take various forms as well known in the prior art, for example, as disclosed in the book COMPUTER GRAPHICS: PRINCIPLES AND PRACTICE, Second Edition, Foley et al., Published by Addison-Wesley Publishing Company, 1991. Specifically see the description at section 4.4 (page 184). Functionally, the video controller 10 is capable of mixing signals representative of different images in accordance with desired formats. In that regard, as indicated above, the video controller 10 also is connected to receive signals representative of another image from a frame buffer 12 driven by a display processor 13 utilizing data from a scan data memory 14. Such elements are well known as described in the above referenced text on computer graphics. As described in greater detail below, the computer graphics elements provide a reference image 15 (right) on the screen 16 of the display device D.

Recapitulating, the screen 16 of the display device displays two images representative respectively of the tissue currently viewed by the camera 6 (image 11, left) and a stored scan data image (reference image 15, right) provided from the memory 14. Note that the reference image 15 (scan data) may be from CT, MRI or other imaging systems and can be provided in stereotactic space relative to the headring structure R by localizer means or other techniques as well known in the art. In that regard, functional apparatus embodying such techniques is available from Radionics, Burlington, Mass. The imaging data from the memory 14 may take the form of raw slice data or angiographic planar images that may be put into stereotactic space relative to the head or ring structure R and the holder 4 and may involve the utilization of "frameless indexing methods" as reported by Drs. B. Guthrie and J. Adler. For example, such registration may involve a digitizing arm or other optical or electromechanical mechanism, as known in the art to register the patient's head H in relation to the ring structure 2 or land marks on the surface of the patient's head. Once such referencing has been done, the imaging data from the memory 14 can be related in space to the patient's head H and any associated nearby apparatus as the headring 2. Thus, the camera 6 can be adjusted in space to point at a view that has been visualized quantitatively or stereotactically in the image scanner database (memory 14). Such is also a form of stereotactic localization.

With the stereotactic data available from the position of the stereotactic localizer, a computer graphics reference image may be provided indicating the view expected in the surgical opening 7. Specifically, the image may take the form of the image 15 as shown in FIG. 1. That reference image, along with its various visualized structures, would then correspond to what the surgeon should see at a given depth of penetration into the surgical opening 7. Thus, by having a direct comparison of the camera vision view image 11 (current actual) next to the reconstructed surgical view image 15 (reference), the surgeon is able to make quantitative and predetermined maneuvers within the opening 7, using instruments that are placed into the opening knowing what critical structures or target structures can be anticipated.

Returning to the imaging system I, the scan data memory 14 provides image data through the display processor 13 to be stored in the frame buffer 12 preliminary to display operations. In that regard, as indicated above, forms of such structures are well known in the graphics art, specifically, see the above-referenced text, COMPUTER GRAPHICS: PRINCIPLES AND PRACTICE. Note that graphic data stored by the memory 14 also may include data for index marks 17, e.g. azimuthal angle registration designations "0" and "180" provided for both images 11 and 15.

It may be necessary to exactly register the dimensions of both images so that they appropriately correspond in size. In that regard, the display processor 13 along with the video controller 10 afford such capabilities. Thus, the system hereof affords a view of the combined, simultaneous images of a camera view with a reconstructed view of the same surgical opening on a common display device.

With the camera 6 placed as shown in FIG. 1, a surgeon can simply view one object, namely the screen 16, without being required to look back at the surgical opening 7 to perform manipulations. For example, a surgeon could place instruments into the surgical opening 7 while viewing the computer screen 16 to view the instruments as they appeared in the image 11. By knowing the depth at which the tools are being manipulated in the surgical opening, the surgeon could compare image 11 with image 15 for reference. A full operation could be performed with such a graphics display view. Thus, the system enables the importation of the surgical field image 11 concurrently with the computer reconstructed image 15.

Figure 2:
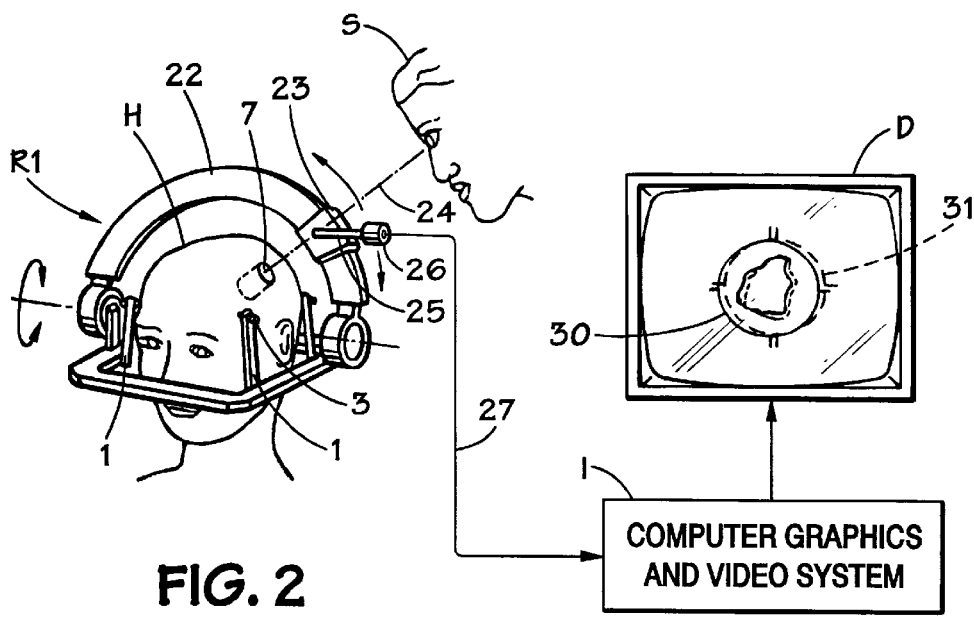
FIG. 2 is another combined perspective and block diagram view showing another embodiment of the present invention.

Turning now to the embodiment of FIG. 2, reference numerals similar to those above are used for similar components. In that regard, note that the imaging system I is shown as a combined structure, that is, simply a single block for processing the signals to drive the display device D.

Generally, the embodiment of FIG. 2 presents a system in accordance herewith that incorporates a more elaborate head frame R1 and is minimally obstructive in directly viewing the surgical opening 7. Again, the headframe R1 is secured to the patient's head H by posts 1 and screws 3. The unit may comprise a stereotactic arc system as for example in the form of a commercially available CRW Stereotactic Instrument produced by Radionics of Burlington, Mass.

An arc 22 of the frame R1 incorporates a probe carrier 23 with the capability to hold instruments or camera devices aligned with a predetermined trajectory 24. Mounted on the probe carrier 23 is a tubular optical system 25 such as is commonly found in endoscopes and which commonly involve either fiber optic or glass lens carriers. The optical system 25 is connected to a camera 26 and in that regard, the optical system 25 can be made of very small diameter so that the degree of obstruction along the line of sight or trajectory 24 is minimal. A connection is provided via a cable 27 from the camera 26 to the computer-graphics and video system I.

An advantage of the embodiment of FIG. 2 is that a surgeon S can view into the surgical opening 7 via the camera 26 or view directly into the opening. Thus, the surgeon S has the option of performing machine/vision procedures exclusively using the visualization images of the display device D, or alternatively he may look directly into the opening 7.

Optical systems such as the system 25 are common in minimally invasive surgery inside the body. Such devices are generally known as endoscopes, and are commonly coupled to cameras. In that regard, endoscopes are always placed into the body through a surgical wound or orifice. However, the embodiment of FIG. 2 differs in that the optical system 25 is external to the body and approximates the opening of the surgical wound 7 so as to view into the surgical opening 7. Thus, the system could be referred to as an extracorporeal analog of an endoscope.

There are many structures and devices for viewing the comparative images of the computer reconstructed data and the video camera. For example, as depicted in FIG. 2, the computer graphics and video system I mixes the two sources of image data to provide superimposed or overlapping images. Specifically, a solid line image 30 represents the actual current image from the camera 26. A dashed line image 31 represents the computer graphics image of the same field provided from scanned memory data.

In addition to superimposition, methods of color transparency and wire frame displays also are well known in computer graphics and could be utilized to enhance images in various formats. Thus, in accordance with various techniques of the art, the two images (images 11 and 15, FIG. 1 and images 30 an 31, FIG. 2) might be variously implemented and displayed. Specifically, for example, liquid crystal displays may be employed.

Figure 3:
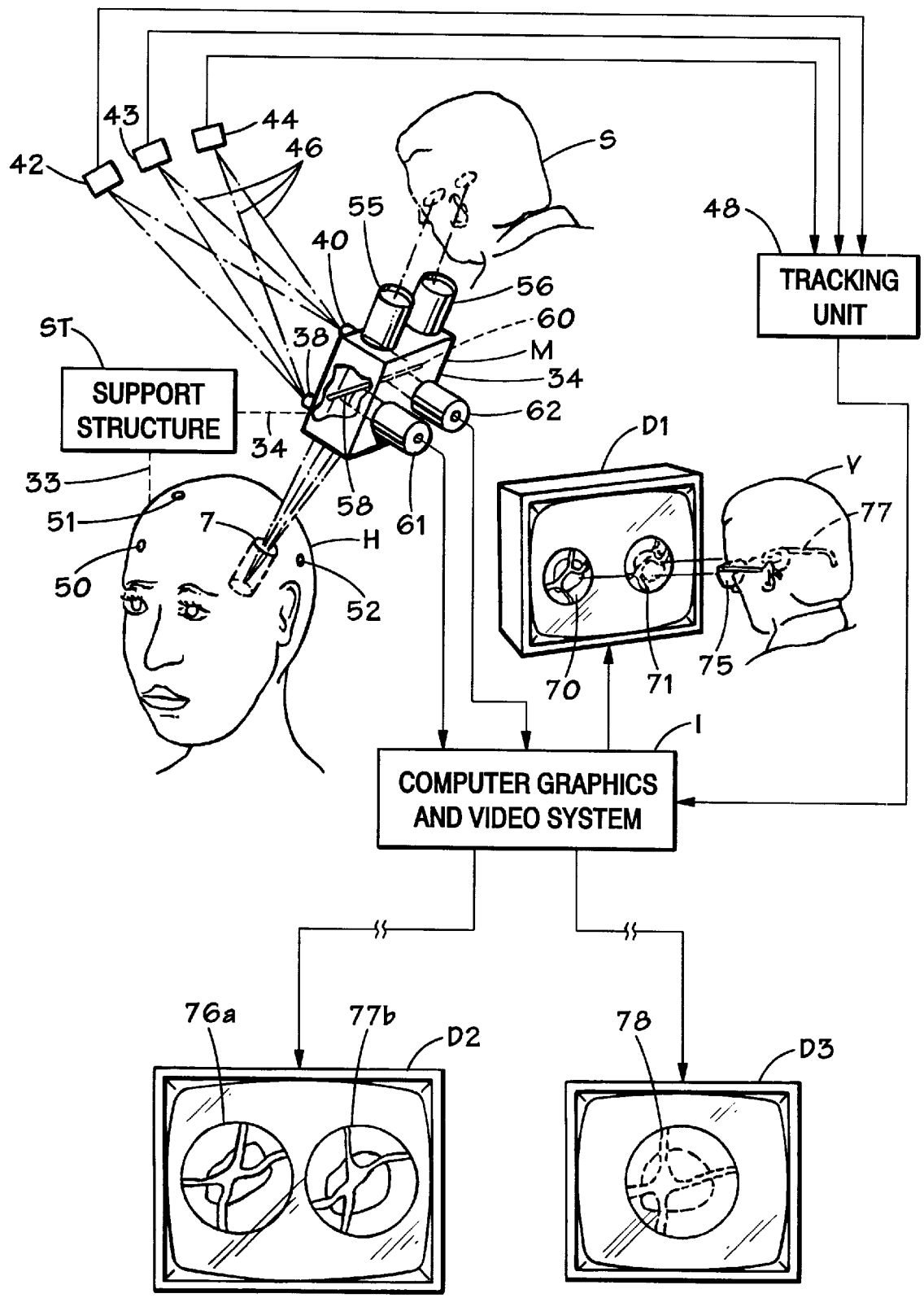
FIG. 3 is still another combined perspective and block diagram view showing still another embodiment of the present invention.

Turning now to FIG. 3, it will be noted that similar reference numerals are again utilized to identify similar components and, again, the computer graphics and video system I (FIG. 1) is represented by a single block.

Generally, in the system of FIG. 3, a surgical microscope is incorporated with camera structure in a composite microscope structure M. The composite structure M is utilized and positionally tracked so as to provide both a camera view and a microscopic view by the surgeon S into the surgical opening 7.

Considering the system of FIG. 3 in somewhat greater detail, the microscope structure M may be variously supported with or without direct reference to the patient's head H. In that regard, a support structure is represented by a block S with dashed lines 33 and 34 extending respectively to the patient's head H and the microscope structure M.

In the system of FIG. 3, the position of the microscope structure M is tracked without the requirement of a physical connection to the patient's head H; however, various devices may be employed as the support structure S and in that regard, the mounting could be on the patient's head H as described with respect to FIGS. 1 and 2. However, in the embodiment of FIG. 3, the position of the microscope structure M is tracked by optical sensing as generally known in the art.

Considering the microscope structure M in greater detail, a housing 34 contains optical elements and supports external apparatus. Specifically, a pair of light emitting diodes 38 and 40 (as shown mounted at the upper end of the housing 34 in FIG. 3) are externally mounted to be viewed by stationary cameras 42, 43, and 44. Consequently, as generally indicated by ray lines 46, each of the cameras 42, 43 and 44 receives infrared radiation from which a determination is made as to the position and orientation of the light emitting diodes 38 and 40, and accordingly, the position and orientation of the microscope structure M. Each of the stationary cameras 42, 43 and 44 is connected to a tracking unit 48, which provides a reference signal to the computer graphics and video system I. In that regard, the cameras 42, 43, and 44 along with the tracking unit 48 may take the form of a commercial implementation known as Pixys' of Nothern Digital tracking system, available from Pixys Inc., located at Boulder, Colo., USA. Thus, the microscope structure M may be registered with reference to the patient's head H. That is, by tracking the position of the microscope structure M and referencing it to the patient's head H, stereotactic operation is accomplished. Specifically, the microscope structure M may be referenced to the patient's head by sequentially focusing it on physical markers 50, 51, and 52 borne on the patient's head H. Thus, by registering the microscope structure M with respect to the patient's head H and tracking it, the resulting data, indicating position and orientation relative to the patient's head, enables the formulation of computer graphics data as described above.

As suggested above, independent of the displayed images, the surgeon S may view the surgical opening 7 directly through the microscope M. In that regard, gazing through the optical viewing ports 55 and 56, the surgeon's lines of sight pass through a pair of beam splitters 58 and 60 to the surgical opening 7. Alternative to such a direct view, consider now the provision of the displayed images as described with reference to earlier embodiments.

The housing 34 carries a pair of video cameras 61 and 62 mounted to view the surgical opening 7 as a reflected image from the beam splitters 58 and 60. Accordingly, the beam splitters enable the cameras 61 and 62 to "look" down the field of the microscope, just as the optical viewing ports 55 and 56 do for the visualization by the surgeon S. Thus, the same view that the surgeon would observe is received by the video cameras 61 and 62 which may provide representative signals for a stereoscopic (three dimensional) view of the surgical scene, e.g., the surgical opening 7.

With the position of the microscope structure M known in relation to the patient's head H, stereotactic coordination or mapping is accomplished as explained above. In that regard, data signals from the cameras 61 and 62 are provided to the computer graphics and video system I for processing to accomplish actual and reference images on the screen 16 of the display unit D. In that regard, the resulting images 70 and 71 may be substantially as previously described; however, in the embodiment of FIG. 3, the image 70 may be stereo optical as indicated above. That is, the image 70 is a video representation of one or both of the camera views from the cameras 61 and 62. Accordingly, various stereooptic techniques may be employed. For example, an alternating flicker view between the cameras 61 and 62 may be provided in synchronism with a viewing device 77 worn by the viewer V to perceive a three-dimensional image. That is, the viewer V wears the viewing device 77 incorporating a pair of eye pieces 75 functioning as synchronized shutters to attain a three dimensional image as well known in the art.

In the display of the screen 16, adjacent images (video image 70, the graphic image 71) are presented. The display is provided by processed signals from the computer graphics and video system I. Data for the graphic image 71 may be developed from stored image information or taken directly from an imaging machine by the utilization of a transfer device as indicated above. Of course, the images 70 and 71 also may be viewed in a non-3D fashion as well if desired and as explained above.

It will be apparent that the surgeon S may look at the computer screen 16 (viewer V) and see the same field of view or a similar field of view that he could view through the microscope structure M. In that regard, as explained above, alternatives include the possibility of utilizing tiny cameras that view into the surgical opening 7 and enable the surgeon to simultaneously view the surgical opening 7 by means of binocular eye pieces or perhaps a standard surgical microscope.

As indicated in FIG. 3, image data also may be sent to separate display units D2 and D3 for providing other displays of images 76a, 77b and 78. Again, these images may be variously formed and constituted. In that regard, the display units D2 and D3 may take the form of very large CRT monitors near a surgical scene or could be smaller monitors mounted near the surgeon or worn by a surgeon as the device 77 coupled to the display unit.

The various displays could be imported even into the microscope itself and viewed with beam splitter structures. Alternatively, the various displays could be imported into commercially available heads-up displays or goggle displays. To further indicate variations, combinations of microscopes, optical viewers, cameras and multiplicities thereof of each of these can be invoked to produce three-dimensional, single-dimensional, or comparative views.

A variety of imaging devices and image scan apparatus can be used to accumulate image data, including CT, MRI, ultrasound, PET scanning, 2-D and/or dynamic angiographic or planar X-ray structures, rendered either in two dimensions or three dimensions. A variety of graphics display structure also may be used including cathode ray tube apparatus, along with 2-D and 3-D viewing methodologies, eye pieces, glasses, etc. Many other implementations of cameras, video mixing and assimilation and three-dimensional computer graphics representation of anatomy may be devised by those skilled in the art.

What is claimed is:

1. An extracorporeal surgical viewing system for displaying coordinated multiple images relating to a surgical opening in a patient's body, said system comprising:

a source of stored scan data representative of a patient's body, said stored scan data being provided in stereotactic space established relative to said patient's body;

a camera system for providing current video signals representative of a viewed subject;

a stereotactic apparatus including means for mounting said camera system in a position to view into the depths of said surgical opening in a patient's body and including means for stereotactically tracking the position of said camera system relative to said stereotactic space established with reference to said patient's body, said stereotactic apparatus including means for releasable substantially rigid attachment to said patient's body, whereby when said stereotactic apparatus is attached to said patient's body and said camera system is mounted on said mounting means, said camera system will be in a known relationship to said stereotactic space used for said stored scan data;

means for providing reference scan data signals from said stored scan data, said reference scan data signals being representative of the patient's body at the location in said stereotactic space viewed by said camera system when mounted on said mounting means; and display apparatus coupled to receive said current video signals from said camera system and said reference scan data signals representative of the patient's body at the location viewed by said camera system to provide a coordinated multiple image display.

2. An extracorporeal surgical viewing system in accordance with claim 1 wherein said stereotactic apparatus includes a head ring adapted to be affixed to said patient and wherein said camera system includes a video camera.

3. An extracorporeal surgical viewing system in accordance with claim 1 wherein said means for providing reference scan data signals from said stored scan data, includes a frame buffer.

4. An extracorporeal surgical viewing system for providing actual and reference images in a coordinated display relating to a surgical opening in a patient's body, said system comprising:

a source of stored reference image scan data representative of the patient's body said reference image scan data being provided in stereotactic space established relative to said patient's body;

a camera system, said camera system being independent of said source of stored reference image scan data for providing video signals representative of a view into the surgical opening in the patient's body;

a stereotactic apparatus releasably attachable to said patient's body, said stereotactic apparatus including means for mounting said camera system in a known position relative to said stereotactic space used for said reference image scan data to provide, when mounted on said stereotactic apparatus, a view of said surgical opening in the patient's body and including means for tracking the position of said camera system in said stereotactic space established with reference to the patient's body;

computer graphics means coupled to said source of stored reference image scan data and to said means for tracking the position of said camera system for providing reference image display data of the patient's body related to the current position of said camera system and representing a reconstructed view corresponding to the view of said camera system of said surgical opening; and display means for processing said video signals from said camera system and said reference image display data of the patient's body related to the current position of said camera system to provide a coordinated display related to said stereotactic space of the view of said camera system and the reconstructed view.

5. An extracorporeal surgical viewing system in accordance with claim 4 wherein said stereotactic apparatus includes a head ring adapted to be affixed to said patient.

6. An extracorporeal surgical viewing system according to claim 4 wherein said camera system includes a microscope.

7. An extracorporeal surgical viewing system according to claim 4, wherein said camera system comprises a pair of cameras to provide video signals representative of a stereoscopic image.

8. An extracorporeal surgical viewing system according to claim 4, wherein said stereotactic apparatus includes light elements affixed to said camera system and sensors for receiving light from said light elements to provide signals indicative of the position and orientation of said camera system to control said computer graphics means.

9. An extracorporeal viewing system according to claim 4, wherein said stereotactic apparatus includes a head frame including a stereotactic arc structure.

10. An extracorporeal viewing system according to claim 4 wherein said camera system includes a camera and wherein said stereotactic apparatus includes a support structure for said camera and physical markers adapted to be placed on said patient for use with said camera to register said camera with respect to the patient thereby tracking the positional relationship of said camera and the patient.

11. An extracorporeal viewing system according to claim 10 wherein said support structure allows movement of said camera and the viewing system further includes a tracking system to provide said computer graphics means with signals indicative of the spatial position of said camera in reference to the patient.

12. An extracorporeal viewing system according to claim 4, wherein said camera system includes a camera and said viewing system further includes a microscope integral with said camera for alternatively viewing said surgical field of the patient's body.

13. An extracorporeal viewing system according to claim 12 further including a beam splitter structure, and wherein said camera, said microscope and said beam splitter structure are affixed together to provide similar views of said surgical field to said camera and said microscope.

14. An extracorporeal viewing system according to claim 12 wherein said camera and said microscope are stereo optical.

15. A process for displaying coordinated multiple images relating to a surgical opening in a patient's body, including the steps of:
    storing scan data representative of the patient's body said stored scan data being provided in stereotactic space established relative to said patient's body;
    mounting a camera system on a support, said support being fixed in a known spatial relationship to said stereotactic space established relative to said patient's body;
    operating said camera system to provide current video signals representative of said depths of said surgical opening;
    tracking the position of said camera system with reference to said stereotactic space established relative to said patient's body as said camera system provides current video signals representative of said depths of said surgical opening;
    providing reference scan data signals from said stored scan data representative of the patient's body at the location viewed by said camera system, said reference scan data signals not being provided by said camera system; and
    displaying multiple images of said depths of said surgical opening in accordance with said current video signals and said reference scan data signals, said multiple images being coordinated with respect to said stereotactic space.

16. A process according to claim 15 wherein said step of providing mounting said camera system includes fixing at least a part of said camera system to said patient's body.

17. A process according to claim 15 wherein said multiple images are displayed in an overlapping relationship.

18. An extracorporeal surgical viewing system for displaying coordinated multiple images relating to a surgical opening in a patient's body, said system compromising:
    a stereotactic apparatus releasably and substantially rigidly attachable to said patient's body,
    a source of stored scan data representative of said patient's body, said stored scan data being provided in stereotactic space established relative to said patient's body;
    a camera system for providing current video signals representative of said surgical opening, said camera system being mounted on said stereotactic apparatus in known dimensional relationship to said stereotactic space, which known dimensional relationship is determinable by said stereotactic apparatus independently of said video signals;
    means for providing reference scan data signals from said stored scan data, said reference scan data signals being representative of said patient's body at the location in said stereotactic space viewed by said camera system; and
    display apparatus coupled to receive said current video signals from said camera system and said reference scan data signals from said source of stored scan data to provide a multiple image display of said reference scan data signals and said current video signals, said multiple image display being coordinated with respect to said stereotactic space.

19. A process for displaying coordinated multiple images related to a surgical opening in a patient's body, said process including the steps of:
    storing scan data, said scan data being representative of said patient's body in stereotactic space established relative to said patient's body;
    mounting a camera system in a position to view said surgical opening and in a known dimensional relationship to said stereotactic space;
    operating said camera system to provide current video signals representative of said surgical opening;
    tracking the position of said camera system with reference to said stereotactic space as said camera system provides current video signals representative of said surgical opening said tracking being performed without utilizing said current video signals;
    providing reference scan data signals from said stored scan data; and
    displaying multiple images of said surgical opening in accordance with said current video signals and said reference scan data signals, said multiple images being coordinated with respect to said stereotactic space.

* * * * *